US009782150B2

(12) United States Patent
Kiyose et al.

(10) Patent No.: US 9,782,150 B2
(45) Date of Patent: Oct. 10, 2017

(54) ULTRASONIC TRANSDUCER DEVICE, PROBE, ELECTRONIC INSTRUMENT, AND ULTRASONIC DIAGNOSTIC DEVICE (71) Applicant: SEIKO EPSON CORPORATION, Tokyo (JP)

(72) Inventors: Kanechika Kiyose, Nagano (JP); Hironori Suzuki, Nagano (JP); Hiroshi Matsuda, Gifu (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 15/417,875

(22) Filed: Jan. 27, 2017

(65) Prior Publication Data
US 2017/0128047 A1    May 11, 2017

Related U.S. Application Data (63) Continuation of application No. 14/227,558, filed on Mar. 27, 2014.

(30) Foreign Application Priority Data

Mar. 29, 2013 (JP) ................................ 2013-071582

(51) Int. Cl.
A61B 8/00 (2006.01)
A61B 8/08 (2006.01)
B06B 1/06 (2006.01)

(52) U.S. Cl.
CPC .......... A61B 8/4494 (2013.01); A61B 8/4427 (2013.01); A61B 8/5207 (2013.01); B06B 1/0688 (2013.01)

(58) Field of Classification Search
None
See application file for complete search history.

(56) References Cited

U.S. PATENT DOCUMENTS

| 4,651,310 | A | 3/1987 | Kaneko et al. |
| 5,142,511 | A | 8/1992 | Kanai et al. |
| 5,852,337 | A | 12/1998 | Takeuchi et al. |
| 2006/0176343 | A1 | 8/2006 | Shimada et al. |

(Continued)

FOREIGN PATENT DOCUMENTS

| JP | 02-253798 A | 10/1990 |
| JP | 08-035954 A | 2/1996 |

(Continued)

OTHER PUBLICATIONS

The Extended European Search Report for the corresponding European Application No. 14162330.6 dated Sep. 29, 2015.

Primary Examiner — Joel F Brutus
(74) Attorney, Agent, or Firm — Global IP Counselors, LLP (57) ABSTRACT An ultrasonic transducer device includes a base, a first electrode film, a piezoelectric film, a second electrode film and a first conductive film. The base has a plurality of vibrating film portions arranged in an array pattern. The first electrode film is disposed on each of the vibrating film portions. The piezoelectric film is disposed on the first electrode film. The second electrode film is disposed on the piezoelectric film. The first conductive film is connected to the first electrode film. The first conductive film has a film thickness larger than a film thickness of the first electrode film.

11 Claims, 8 Drawing Sheets (56) References Cited

U.S. PATENT DOCUMENTS

| | | |
|---|---|---|
| 2006/0290747 A1 | 12/2006 | Shimada et al. |
| 2009/0156083 A1 | 6/2009 | Nakazawa et al. |
| 2011/0012478 A1* | 1/2011 | Najafi .................. B81C 1/0019 310/334 |
| 2011/0115337 A1 | 5/2011 | Nakamura et al. |
| 2011/0221306 A1 | 9/2011 | Matsuda |

FOREIGN PATENT DOCUMENTS

| | | |
|---|---|---|
| JP | 08-088899 A | 4/1996 |
| JP | 2001-291907 A | 10/2001 |
| JP | 2005-051688 A | 2/2005 |
| JP | 2006-198996 A | 8/2006 |
| JP | 2006-231909 A | 9/2006 |
| JP | 2007-175989 A | 7/2007 |
| JP | 2010-042683 A | 2/2010 |
| JP | 2013-046086 A | 3/2013 |
| WO | 2005/028207 A1 | 3/2005 |

* cited by examiner

Fig. 11

ULTRASONIC TRANSDUCER DEVICE, PROBE, ELECTRONIC INSTRUMENT, AND ULTRASONIC DIAGNOSTIC DEVICE

CROSS-REFERENCE TO RELATED APPLICATIONS

This application is a continuation application of U.S. patent application Ser. No. 14/227,558 filed on Mar. 27, 2014. This application claims priority to Japanese Patent Application No. 2013-071582 filed on Mar. 29, 2013. The entire disclosures of U.S. patent application Ser. No. 14/227,558 and Japanese Patent Application No. 2013-071582 are hereby incorporated herein by reference.

BACKGROUND

Technical Field

The present invention relates to an ultrasonic device as well as a probe, electronic instrument, ultrasonic image device and the like that uses that.

Related Art

Ultrasonic transducer devices are generally known. For example, with the ultrasonic transducer device noted in Japanese Unexamined Patent Publication No. 2005-51688, a plurality of vibrating films are provided in an array pattern. A lower electrode is formed on the vibrating film. Wiring is connected to the lower electrode. The lower electrode and wiring are covered by a piezoelectric film. An upper electrode is formed on the piezoelectric film.

SUMMARY

It is desirable for the piezoelectric film to be divided for each vibrating film. For example, it is possible to have the piezoelectric element formed individually for each vibrating film instead of the full coverage piezoelectric film noted in Japanese Unexamined Patent Publication No. 2005-51688. In this case, according to a typical method, a piezoelectric body for a piezoelectric element is formed from a full coverage material film using etching processing. The wiring is exposed by the etching process. The wiring film thickness is reduced. Furthermore, when the top part electrode is formed, the wiring is exposed by the etching process. With this kind of film thickness decrease, the wiring electrical resistance becomes higher.

According to at least one aspect of the present invention, it is possible to provide an ultrasonic transducer device that avoids a rise in wiring resistance while having a piezoelectric film for each vibrating film.

An ultrasonic transducer device according to one aspect includes a base, a first electrode film, a piezoelectric film, a second electrode film and a first conductive film. The base has a plurality of vibrating film portions arranged in an array pattern. The first electrode film is disposed on each of the vibrating film portions. The piezoelectric film is disposed on the first electrode film. The second electrode film is disposed on the piezoelectric film. The first conductive film is connected to the first electrode film. The first conductive film has a film thickness larger than a film thickness of the first electrode film.

Ultrasonic waves act on the vibrating film. Ultrasonic waves cause ultrasonic vibration of the vibrating film. Current is output from the piezoelectric element according to the ultrasonic vibration of the vibrating film. In this way, the ultrasonic transducer device detects ultrasonic waves. Here, the first conductive film functions as a wiring film of the first electrode film. It is possible to ensure sufficient film thickness for the first conductive film, so it is possible to avoid an increase in wiring resistance. Therefore, it is possible to sufficiently ensure ultrasonic wave detection sensitivity.

The ultrasonic transducer device as described above preferably further includes a second conductive film connected to the first conductive film and separated from the second electrode film, and covers at least a portion of the piezoelectric film.

The ultrasonic transducer device as described above preferably further includes an insulating film disposed between the second electrode film and the second conductive film on the piezoelectric film. Since the second conductive film is separated from the second electrode film, a gap is formed between the second conductive film and the second electrode film. The insulating film inhibits the infiltration of moisture into the gap. As a result, even if the ultrasonic transducer device is exposed to moisture, it is possible to avoid electrical shorts between the second electrode film and the second conductive film.

In the ultrasonic transducer device as described above, a film thickness of the second electrode film and a film thickness of the second conductive film are preferably substantially equal. It is possible for the second electrode film and the second conductive film to be formed from one layer of conductive film. Therefore, it is possible to form the second electrode film and the second conductive film using a shared manufacturing process. It is possible to simplify the manufacturing process.

In the ultrasonic transducer device as described above, the first conductive film preferably has a first direction conductive body part disposed between the first electrode film and a first direction end part of a corresponding one of the vibrating film portion in a plan view as viewed along a thickness direction of the base, and a second direction conductive body part disposed between the first electrode film and a second direction end part of the corresponding one of the vibrating film portions in the plan view, the second direction end part being on an opposite side from the first direction end part, the first electrode film being disposed between the first direction conductive body part and the second direction conductive body part in the plan view. The second conductive film preferably has a first upper layer conductive body part connected to the first direction conductive body part and separated from the second electrode film on the piezoelectric film, and a second upper layer conductive body part connected to the second direction conductive body part and separated from the second electrode film on the piezoelectric film. On the piezoelectric film, a first insulating film is preferably disposed between the second electrode film and the first upper layer conductive body part and a second insulating film is preferably disposed between the second electrode film and the second upper layer conductive body part, and the first insulting film and the second insulating film are preferably separated on the second electrode film.

The first insulating film and the second insulating film inhibit the infiltration of moisture in the gap between the first upper layer conductive body part and the second electrode film, and in the gap between the second upper layer conductive body part and the second electrode film. As a result, even when the ultrasonic transducer device is exposed to moisture, it is possible to avoid electrical shorts between the second electrode film and the first upper layer conductive body part and between the second electrode film and the second upper layer conductive body part. In fact, on the second electrode film, expansion of the first insulating film and the second insulating film is suppressed, so the vibrating film flexibility is maintained well. Therefore, it is possible to maintain the ultrasonic wave detection sensitivity.

It is possible to use any of the ultrasonic transducer devices incorporated in a probe. The probe can be equipped with the ultrasonic transducer device and a case supporting the ultrasonic transducer device.

The ultrasonic transducer device can be used incorporated in an electronic instrument. The electronic instrument can be equipped with the ultrasonic transducer device, and a processing unit connected to the ultrasonic transducer device, and configured to process the output of the ultrasonic transducer device.

The ultrasonic transducer device can be used incorporated in an ultrasonic image device. The ultrasonic image device can be equipped with the ultrasonic transducer device, a processing unit connected to the ultrasonic transducer device and configured to process the output of the ultrasonic transducer device and generate an image, and a display device configured to display the image.

A manufacturing method of an ultrasonic transducer device according to another aspect includes: forming a first material film including a conductive material on a surface of a plurality of vibrating film portions arranged in an array pattern in a base; forming, from the first material film, a first electrode film and at least a portion of a first conductive film continuous from the first electrode film; forming a second material film including a piezoelectric material on the first electrode film and performing patterning processing including etching processing of the second material film to form a piezoelectric film on the first electrode film; forming a third material film including a conductive material to cover surfaces of the first conductive film and the piezoelectric film; and performing patterning processing including etching processing of the third material film to form a second electrode film on the piezoelectric film and a second conductive film separated from the second electrode film on the piezoelectric film and connected to the first conductive film.

Etching processing is implemented when forming the piezoelectric film. At this time, in the periphery of the piezoelectric film, the first conductive film is exposed by the etching process. As a result, the film thickness of the first conductive film is reduced compared to the first electrode film. After that, a third material film is layered on the first conductive film. In this way, the film thickness of the first conductive film increases. It is possible to ensure a sufficient film thickness for the wiring film connected to the first electrode film. It is possible to avoid an increase in wiring resistance. Therefore, it is possible to sufficiently ensure ultrasonic wave detection sensitivity.

BRIEF DESCRIPTION OF THE DRAWINGS

Referring now to the attached drawings which form a part of this original disclosure.

DETAILED DESCRIPTION OF EXEMPLARY EMBODIMENTS

Following, embodiments of the present invention will be explained with reference to the attached drawings. The embodiments explained below shall not be construed as unreasonably limiting the subject matter of the present invention described in the claims, and all the elements explained in the embodiments are not necessarily essential to the solving means of the present invention.

(1) Overall Configuration of Ultrasonic Diagnostic Device

Figure 1:
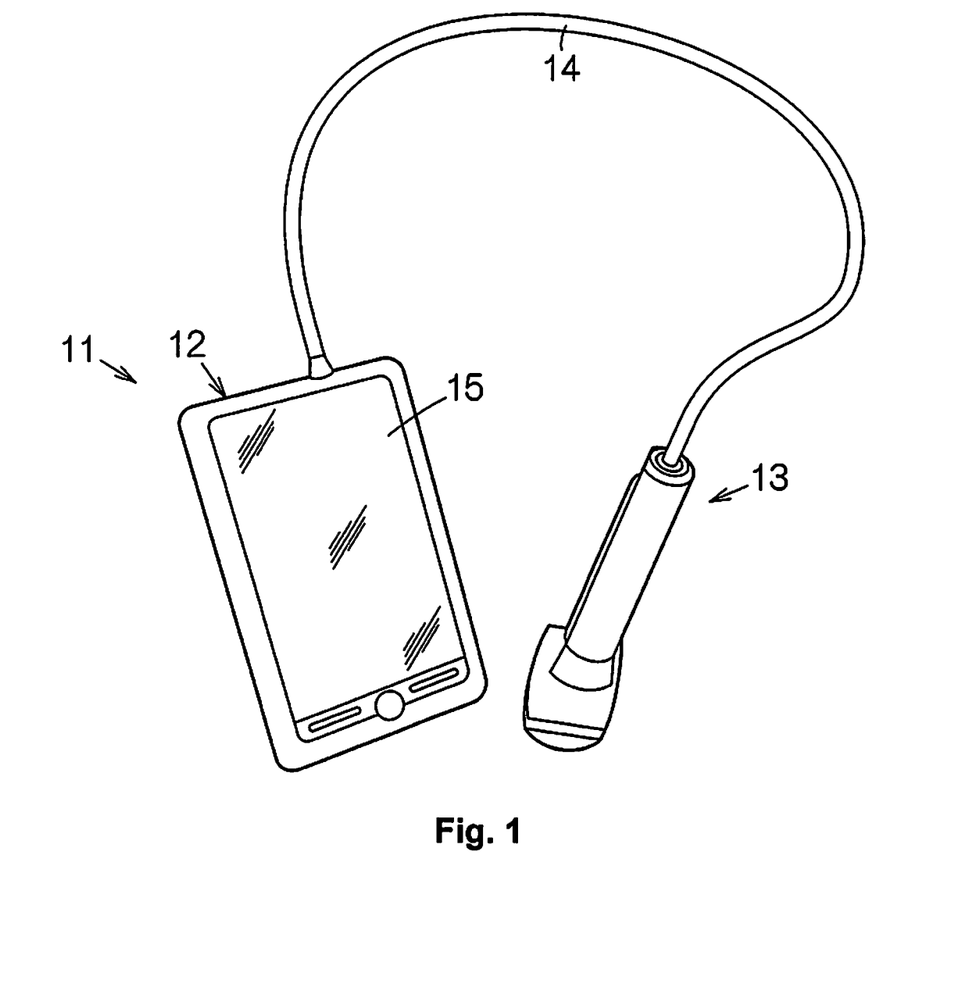
FIG. 1 is an external view schematically showing an example of an electronic instrument, that is, an ultrasonic diagnostic device according to one embodiment.

FIG. 1 schematically shows a configuration of a specific example of an electronic instrument, specifically, an ultrasonic diagnostic device 11, according to an embodiment of the present invention. The ultrasonic diagnostic device 11 is provided with a device terminal 12 and an ultrasonic probe (probe) 13. The device terminal 12 and the ultrasonic probe 13 are connected to each other through a cable 14. The device terminal 12 and the ultrasonic probe 13 exchange electric signals through the cable 14. A display panel (display device) 15 is incorporated in the device terminal 12. A screen of the display panel 15 is exposed on a surface of the device terminal 12. As described later, in the device terminal 12, an image is generated based on ultrasonic waves detected with the ultrasonic probe 13. Imaged detection results are displayed on the screen of the display panel 15.

Figure 2:
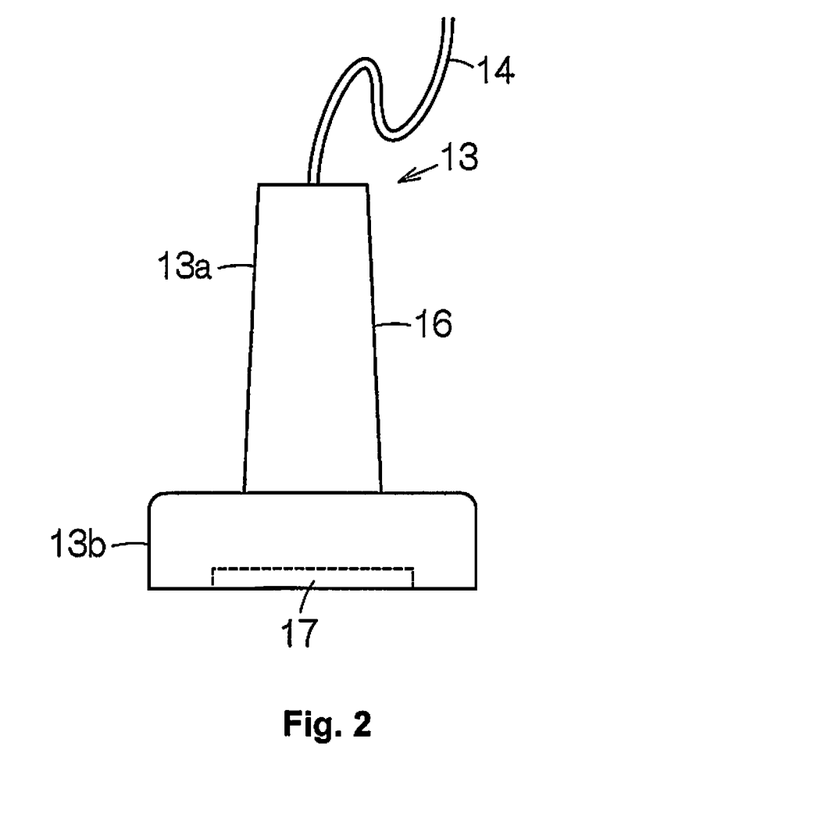
FIG. 2 is an enlarged front view of an ultrasonic probe.

As shown in FIG. 2, the ultrasonic probe 13 has a case 16. An ultrasonic transducer element unit (hereinafter referred to as "element unit") 17 is housed in the case 16. The ultrasonic transducer element unit 17 is a specific example of an ultrasonic transducer device, according to an embodiment of the present invention. A surface of the element unit 17 may be exposed on a surface of the case 16. The element unit 17 outputs ultrasonic waves from the surface thereof, and receives reflected waves of ultrasonic waves. In addition, the ultrasonic probe 13 can be equipped with a probe head 13b linked to be freely attachable and detachable with the probe main unit 13a. At this time, the element unit 17 can be incorporated inside the case 16 of the probe head 13b.

Figure 3:
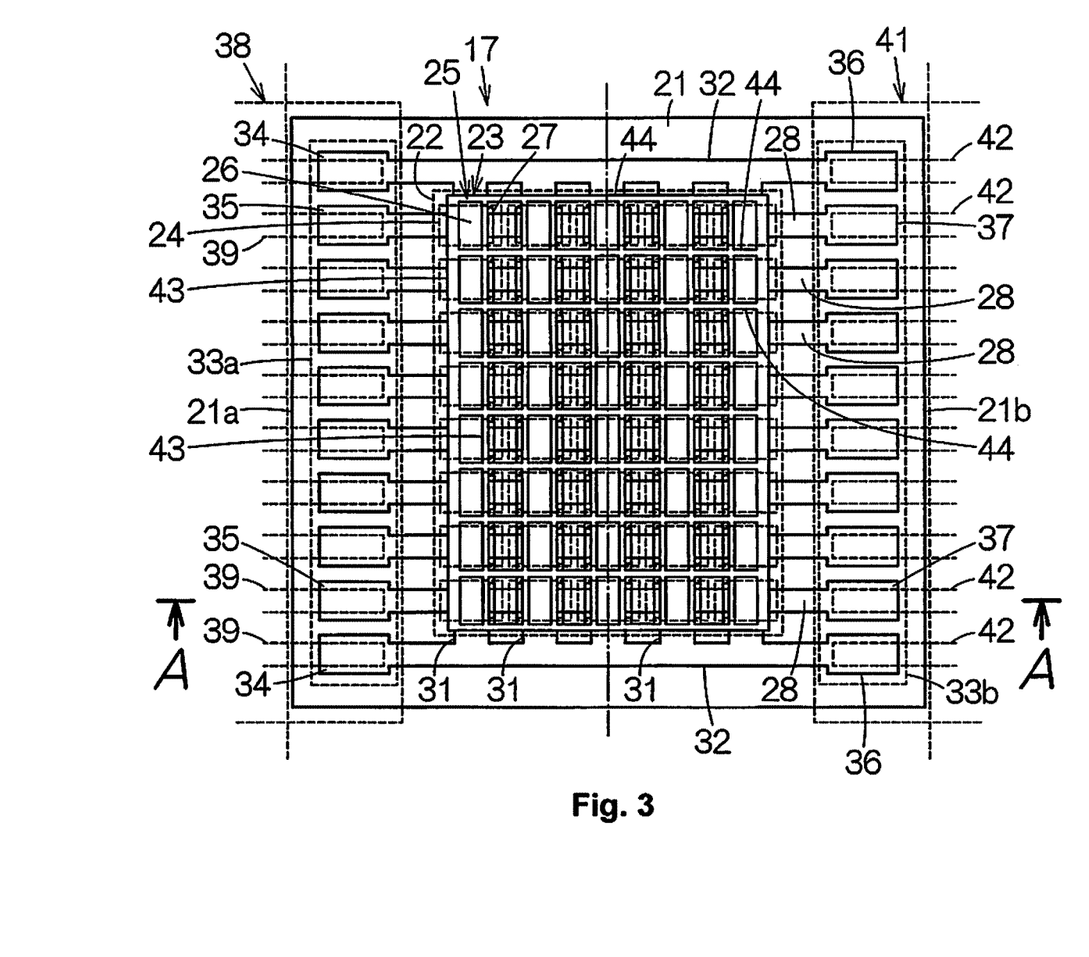
FIG. 3 is an enlarged plan view of an ultrasonic transducer element unit according to the first embodiment.

FIG. 3 schematically shows a plan view of the element unit 17 according to an embodiment. The element unit 17 is provided with a base 21. An element array 22 is formed on the base 21. The element array 22 is constructed of ultrasonic transducer elements (hereinafter referred to as "elements") 23 arranged in an array pattern. The array is formed in a matrix having a plurality of rows and a plurality of columns. In addition, a zigzag pattern may be used in the array. In the zigzag pattern, a group of the elements 23 in an even column may be displaced with respect to a group of the elements 23 in an odd column by one-half of the row pitch. The number of the elements in one of an odd column and an even column may be smaller than the number of the elements in the other of an odd column and an even column by one.

Each element 23 is equipped with a vibrating film 24. Details of the vibrating film 24 are described later. In FIG. 3, the outline of the vibrating film 24 is depicted with a dotted line with a plan view in the direction orthogonal to the film surface of the vibrating film 24 (plan view in the substrate thickness direction). The inside of the outline correlates to the area interior of the vibrating film 24. The outside of the outline correlates to the area exterior of the vibrating film 24. A piezoelectric element 25 is formed on the vibrating film 24. As described later, with the piezoelectric element 25, a piezoelectric film (not illustrated) is sandwiched between an upper electrode (second electrode) 26 and a lower electrode (first electrode) 27. These are layered in sequence. The element unit 17 is constituted as one ultrasonic transducer element chip.

A plurality of first conductive bodies 28 are formed on the surface of the base 21. The first conductive bodies 28 extend parallel to each other in the column direction of the array. One conductive body 28 is allocated for each element 23 of one column. One first conductive body 28 is arranged in common with elements 23 aligned in the column direction of the array. The first conductive bodies 28 form the lower electrode 27 for each of the elements 23. In this way, the first conductive bodies 28 are arranged in the vibrating film 24 area interior and area exterior. For the first conductive body 28, it is possible to use a layered film of titanium (Ti), iridium (Ir), platinum (Pt), and titanium (Ti), for example. However, it is also possible to use other conductive materials for the first conductive body 28.

A plurality of second conductive bodies 31 are formed on the surface of the base 21. The second conductive bodies 31 extend parallel to each other in the row direction of the array. One second conductive body 31 is allocated to each element 23 of one row. The one second conductive body 31 is connected in common to the elements 23 aligned in the row direction of the array. The second conductive bodies 31 form the upper electrode 26 for each of the elements 23. Both ends of the second conductive body 31 are respectively connected to a pair of extraction wirings 32. The extraction wirings 32 extend parallel to each other in the column direction of the array. Therefore, all of the second conductive bodies 31 have the same length. In this way, the upper electrodes 26 are connected in common to the elements 23 of the entire matrix. In this way, the second conductive bodies 31 are arranged in the vibrating film 24 area interior and area exterior. The second conductive body 31 can be formed using iridium (Ir), for example. However, it is also possible to use other conductive materials for the first conductive body 28.

Power distribution of the elements 23 is switched per column. Linear scanning or sector scanning is achieved corresponding to such switching of power distribution. Since the elements 23 in one column output ultrasonic waves at the same time, the number of the elements 23 in one column, that is, the number of rows of the array can be determined based on the output level of ultrasonic waves. For example, the number of rows may be set to be around 10 to 15 rows. In the drawing, five rows are illustrated for simplicity. The number of columns of the array can be determined based on the extent of an area to be scanned. For example, the number of columns may be set to be 128 columns or 256 columns. In the drawing, eight columns are illustrated for simplicity. The role of the upper electrode 26 and the lower electrode 27 can also be switched. Specifically, while the lower electrode is connected in common to the elements 23 of the entire matrix, the upper electrode can be connected in common for each column of the array.

The outline of the base 21 has a first side 21a and a second side 21b that are opposed and partitioned by a pair of straight lines in parallel to each other. One line of a first terminal array 33a is arranged between the first side 21a and the outline of the element array 22. One line of a second terminal array 33b is arranged between the second side 21b and the outline of the element array 22. For the first terminal array 33a, one line can be formed in parallel to the first side 21a. For the second terminal array 33b, one line can be formed in parallel to the second side 21b. The first terminal array 33a is constructed of a pair of upper electrode terminals 34 and a plurality of lower electrode terminals 35. Similarly, the second terminal array 33b is constructed of a pair of upper electrode terminals 36 and a plurality of lower electrode terminals 37. Upper electrode terminals 34 and 36 are respectively connected to both ends of one extraction wiring 32. It is sufficient for the extraction wirings 32 and the upper electrode terminals 34 and 36 to be formed plane-symmetrically with respect to a vertical plane that bisects the element array 22. Lower electrode terminals 35 and 37 are respectively connected to both ends of one second conductive body 31. It is sufficient for the second conductive bodies 31 and the lower electrode terminals 35 and 37 to be formed plane-symmetrically with respect to the vertical plane that bisects the element array 22. The outline of the base 21 is formed to be a rectangle. The outline of the base 21 may be a square or a trapezoid.

A first flexible printed wiring board (hereinafter referred to as "first wiring board") 38 is coupled to the base 21. The first wiring board 38 covers the first terminal array 33a. Conductive lines, that is, first signal lines 38 are formed at one end of the first wiring board 38 corresponding to the upper electrode terminals 34 and the lower electrode terminals 35, respectively. The first signal lines 38 are respectively opposed to the upper electrode terminals 34 and the lower electrode terminals 35, and respectively bonded thereto. Similarly, a second flexible printed wiring board (hereinafter referred to as "second wiring board") 41 covers the base 21. The second flex 41 covers the second terminal array 32b. Conductive lines, that is, second signal lines 42 are formed at one end of the second wiring board 41 corresponding to the upper electrode terminals 36 and the lower electrode terminals 37, respectively. The second signal lines 42 are respectively opposed to the upper electrode terminals 36 and the lower electrode terminals 37, and respectively bonded thereto.

An electrode separation film 43 is arranged in parallel to the second conductive body 31 on the vibrating film 24. The electrode separation film 43 extends in band form in the lengthwise direction of the second conductive body 31. The electrode separation film 43 has insulation properties and moisture proof properties. The electrode separation film 43 is formed from a moisture proof insulating material such as alumina ($Al_2O_3$), silicon oxide ($SiO_2$) or the like, for example. The electrode separation film 43 is formed sandwiching each second conductive body 31 and separated at both sides of the second conductive body 31. The second conductive body 31 intersects the first conductive body 28 on the vibrating film 24, so the electrode separation film 43 crosses over the first conductive body 28 on the vibrating film 24.

An insulating film 44 is formed at the vibrating film 24 area exterior on the base 21. The insulating film 44 extends in band form in the lengthwise direction of the first conductive body 28. The insulating film 44 is arranged in parallel with the first conductive body 28. The insulating film 44 is formed from an insulating material with moisture proof properties such as alumina or silicon oxide, for example. The material of the insulating film 44 is sufficient as long as it matches the material of the electrode separation film 43. The insulating film 44 crosses over the second conductive body 31. In this way, the insulating film 44 is formed on the second conductive body 31. The insulating film 44 is continuous with the electrode separation film 43. The insulating film 44 is connected to the electrode separation film 43 sandwiching the second conductive body 31 and arranged at both sides of the second conductive body 31.

Figure 4:
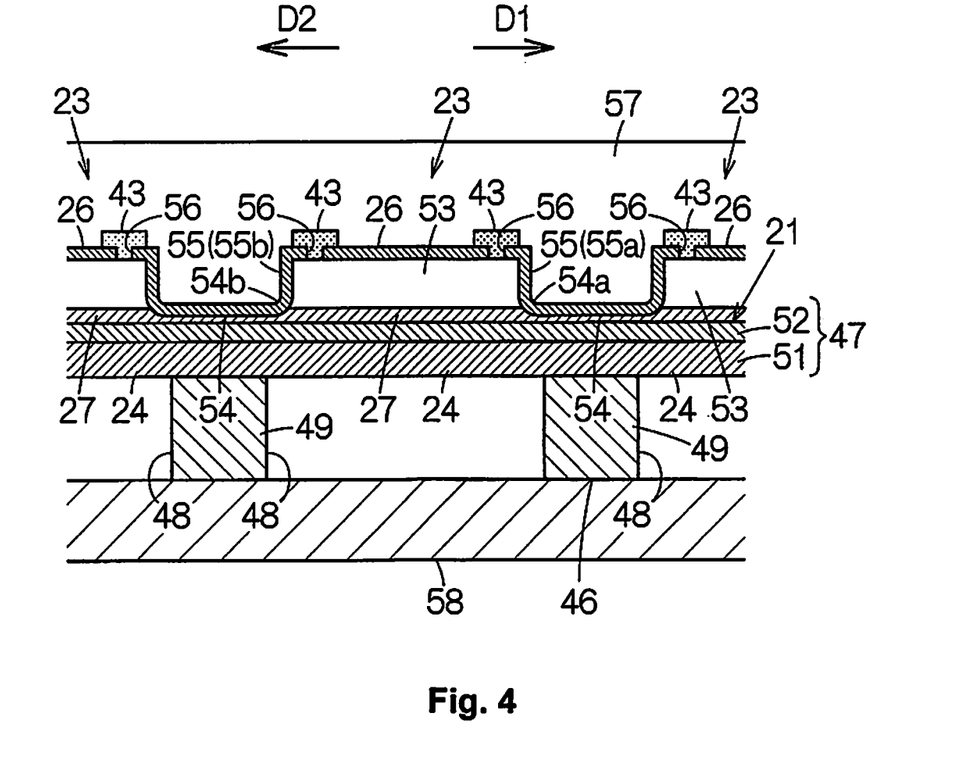
FIG. 4 is a schematic cross section view along line A-A of FIG. 3.

As shown in FIG. 4, the base 21 is equipped with a substrate 46 and a flexible film 47. The flexible film 47 is formed on the entire surface on the surface of the substrate 46. An opening 48 is formed in each of the elements 23 on the substrate 46. The openings 48 are arranged in an array pattern on the substrate 46. The outline of the area in which the openings 48 are arranged correlates to the outline of the element array 22. A partition wall 49 divides between two adjacent openings 48. The adjacent openings 48 are partitioned by the partition wall 49. The wall thickness of the partition wall 49 correlates to the gap of the openings 48. The partition wall 49 defines two wall surfaces on the inside of the plane that expand parallel to each other. The wall thickness correlates to the distance between the two wall surfaces. Specifically, the wall thickness can be defined as the length of the vertical line orthogonal to the wall surface and sandwiched between the wall surfaces.

The flexible film 47 is constructed of a silicon oxide ($SiO_2$) layer 51 layered on the surface of the substrate 46, and a zirconium oxide ($ZrO_2$) layer 52 layered on a surface of the silicon oxide layer 51. The flexible film 47 contacts the openings 48. In this manner, a part of the flexible film 47 corresponding to the outline of the opening 48 forms the vibrating film 24. Of the flexible film 47, the vibrating film 24 is the part that is able to do film vibration in the thickness direction of the substrate 46 since it opposes the opening 48. The film thickness of the silicon oxide layer 51 can be determined based on the resonance frequency.

The first conductive body 28, the piezoelectric film 53, and the upper electrode 26 are layered on a surface of the vibrating film 24 in this order. The piezoelectric film 53 may be formed of piezoelectric zirconate titanate (PZT), for example. Here, the first conductive body 28 has a lower electrode 27 and a first conductive film 54. The first conductive film 54 is connected to the lower electrode 27. The first conductive film 54 is continuous with the lower electrode 27. The film thickness of the first conductive film 54 is greater than the film thickness of the lower electrode 27. A second conductive film 55 is connected to the first conductive film 54. The second conductive film 55 extends over the piezoelectric film 53 branched from the first conductive film 54, and is interrupted at a position separated from the upper electrode 26. For one lower electrode 27, the first conductive film 54 has a first direction conductive body part 54a formed between the lower electrode 27 and the end part of first direction D1 of the vibrating film 24 (hereinafter referred to as "first direction end part"), and a second direction conductive body part 54b formed between the lower electrode 27 and the end part of the second direction D2 (hereinafter referred to as "second direction end part") sandwiching the lower electrode 27 and on the side facing opposite the first direction end part. The second conductive film 55 has a first upper layer conductive body part 55a connected to the first direction conductive body part 54a and separated from the upper electrode 26 on the piezoelectric film 53, and a second upper layer conductive body part 55b connected to the second direction conductive body part 54b and separated from the upper electrode 26 on the piezoelectric film 53. A gap 56 is formed between the upper electrode 26 and the first upper layer conductive body part 55a on the top surface of the piezoelectric film 53, and the gap 56 is formed between the upper electrode 26 and the second upper layer conductive body part 55b.

As shown in FIG. 4, the electrode separation film 43 is formed between the upper electrode 26 and the first upper layer conductive body part 55a. Similarly, the electrode separation film 43 is formed between the upper electrode 26 and the second upper layer conductive body part 55b. The electrode separation film 43 plugs the gap 56 on the top surface of the piezoelectric film 53. The electrode separation film 43 fills in the gap 56. In this way, the surface of the piezoelectric film 53 is covered by the electrode separation film 43 between the upper electrode 26 and the second conductive film 55. Here, the electrode separation film 43 stays inside the area of the vibrating film 24 in the lengthwise direction of the first conductive body 28. The electrode separation film 43 does not affect the edge of the vibrating film 24.

A protective film 57 is layered on the surface of the base 21. The protective film 57 covers the surface of the base 21 across the entire surface, for example. As a result, the element array 22, the first and second terminal arrays 33a and 33b, and the first and second wiring boards 38 and 41 are covered by the protective film 57. For the protective film 57, for example, a silicone resin film can be used. The protective film 57 protects the structure of the element array 22, the bonding of the first terminal array 33a and the first wiring board 38, and the bonding of the second terminal array 33b and the second wiring board 41.

A reinforcing plate 58 is fixed to a reverse surface of the base 21. The reverse surface of the base 21 is overlapped on a surface of the reinforcing plate 58. The reinforcing plate 58 closes the openings 48 in the reverse surface of the element unit 17. The reinforcing plate 58 may have a rigid base material. For example, the reinforcing plate 58 may be formed of a silicon base plate. The plate thickness of the base 21 is set to be around 100 μm, for example, and the plate thickness of the reinforcing plate 58 is set to be around 100 to 150 μm, for example. The partition walls 49 are bonded to the reinforcing plate 58. The reinforcing plate 58 is bonded to each partition wall 49 in at least one bonding area location. For bonding, an adhesive agent can be used.

(2) Circuit Configuration of Ultrasonic Diagnostic Device

Figure 5:
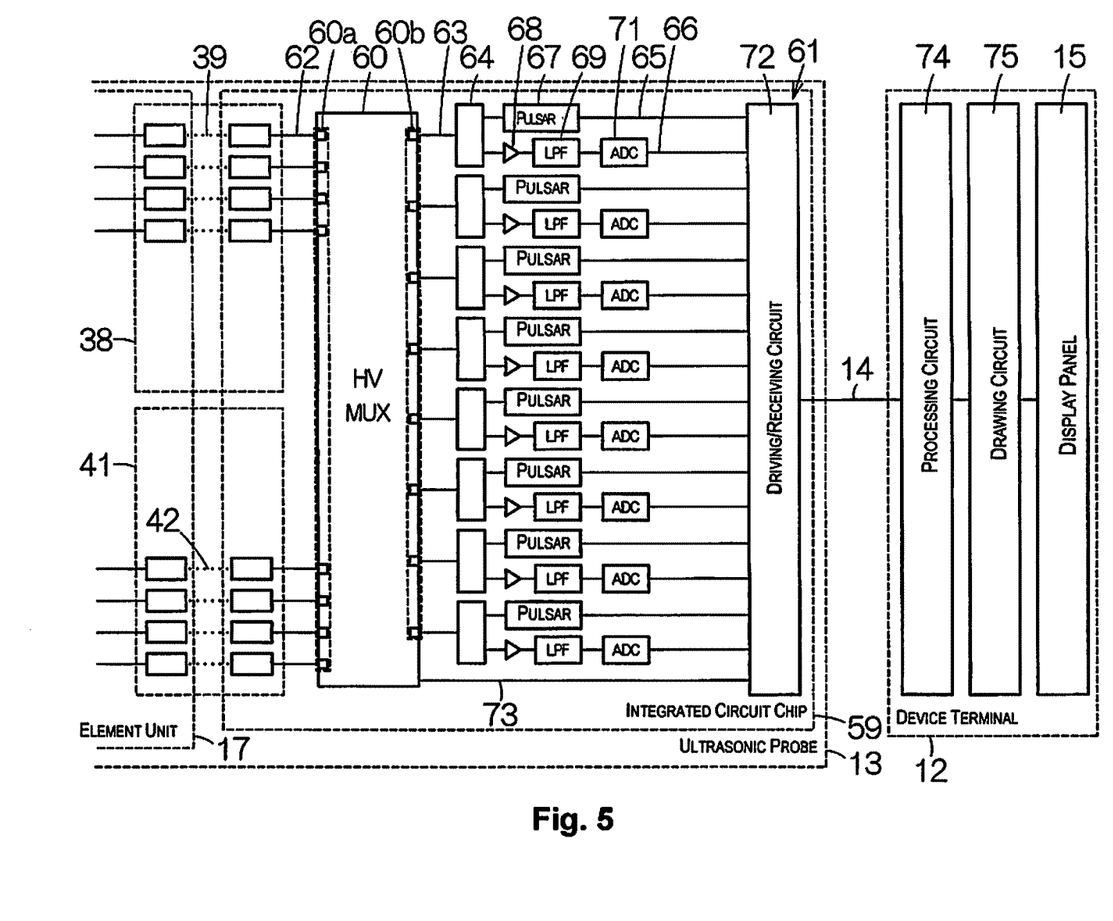
FIG. 5 is a block diagram schematically showing the circuit configuration of the ultrasonic diagnostic device.

As shown in FIG. 5, the ultrasonic diagnostic device 11 is equipped with an integrated circuit chip 59 electrically connected to the element unit 17. The integrated circuit chip 59 is equipped with a multiplexer 60 and a transmitting and receiving circuit 61. The multiplexer 60 has a group of ports 60a on the element unit 17 side, and a group of ports 60b on the transmitting and receiving circuit 61 side. The first signal lines 38 and the second signal lines 42 are connected to the group of ports 60a on the element unit 17 side via a wiring

62. In this manner, the group of ports 60a is connected to the element array 22. Here, a prescribed number of signal lines 63 within the integrated circuit chip 55 are connected to the group of ports 60b on the transmitting and receiving circuit 61 side. The prescribed number corresponds to a column number of the elements 23 output at the same time as scanning is conducted. The multiplexer 60 controls interconnection between the ports on the cable 14 side and the ports on the element unit 17 side.

The transmitting and receiving circuit 61 has a prescribed number of changing switches 64. The changing switches 64 are connected to the corresponding signal lines 63, respectively. The transmitting and receiving circuit 61 has a transmission channel 65 and a reception channel 66 for each of the changing switches 64. The transmission channel 65 and the reception channel 66 are connected to the changing switch 64 in parallel. The changing switch 64 selectively connects the transmission channel 65 or the reception channel 66 to the multiplexer 60. Pulsars 67 are incorporated in the transmission channel 65. The pulsars 67 output a pulse signal at a frequency corresponding to the resonance frequency of the vibrating film 24. An amplifier 68, a low-pass filter (LPF) 69, and an analog-digital converter (ADC) 71 are incorporated in the reception channel 66. The output signal of each of the elements 23 is amplified, and converted into a digital signal.

The transmitting and receiving circuit 61 has a driving/receiving circuit 72. The transmission channel 65 and the reception channel 66 are connected to the driving/receiving circuit 72. The driving/receiving circuit 72 controls the pulsars 67 simultaneously depending on the state of scanning. The driving/receiving circuit 72 receives a digital signal of an output signal depending on the state of scanning. The driving/receiving circuit 72 is connected to the multiplexer 60 through a control line 73. The multiplexer 60 conducts control of interconnection based on a control signal supplied from the driving/receiving circuit 72.

A processing circuit (processing unit) 74 is incorporated in the device terminal 12. The processing circuit 74 can be provided with a central processing unit (CPU) and a memory, for example. The entire operation of the ultrasonic diagnostic device 11 is controlled in accordance with processing of the processing circuit 74. The processing circuit 74 controls the driving/receiving circuit 72 in accordance with instructions input by a user. The processing circuit 74 generates an image in accordance with an output signal of the element 23. The image is specified by drawing data.

A drawing circuit 75 is incorporated in the device terminal 12. The drawing circuit 75 is connected to the processing circuit 74. The display panel 15 is connected to the drawing circuit 75. The drawing circuit 75 generates a driving signal in accordance with drawing data generated in the processing circuit 74. The driving signal is sent to the display panel 15. As a result, an image is displayed on the display panel 15.

(3) Operation of Ultrasonic Diagnostic Device

Next, the operation of the ultrasonic diagnostic device 11 will be explained briefly. The processing circuit 74 gives the driving/receiving circuit 72 instructions to transmit and receive ultrasonic waves. The driving/receiving circuit 72 supplies a control signal to the multiplexer 60, and supplies a driving signal to each of the pulsars 67. The pulsars 67 output pulse signals in response to the supply of the driving signal. The multiplexer 60 connects the port of the group of ports 60a to the port of the group of ports 60b in response to the instructions of the control signal. The pulse signals are supplied to the elements 23 per column through the upper electrode terminals 34 and 36 and the lower electrode terminals 35 and 37 according to the selection of the port. The vibrating film 24 vibrates in response to the supply of the pulse signals. As a result, desired ultrasonic wave beams are emitted toward a target (for example, the inside of a human body).

After ultrasonic waves are transmitted, the changing switch 64 is switched. The multiplexer 60 maintains the connection relation of the ports. The changing switch 64 establishes a connection between the reception channel 66 and the signal line 63 instead of a connection between the transmission channel 65 and the signal line 63. Reflected waves of ultrasonic waves vibrate the vibrating film 24. As a result, an output signal is output from the element 23. The output signal is converted into a digital signal, and sent to the driving/receiving circuit 72.

Transmission and reception of ultrasonic waves are repeated. For this repetition, the multiplexer 60 changes the connection relation of the ports. As a result, linear scanning or sector scanning is achieved. When scanning is finished, the processing circuit 74 generates an image based on the digital signals of the output signals. The generated image is displayed on the screen of the display panel 15.

The ultrasonic waves act on the vibrating film 24. The ultrasonic waves cause ultrasonic vibration of the vibrating film 24. Current is output from the piezoelectric element 25 according to the ultrasonic vibration of the vibrating film 24. In this way, each element 23 detects ultrasonic waves. Here, the first conductive film 54 functions as a wiring film of the lower electrode 27. It is possible to ensure sufficient film thickness for the first conductive film 54. It is possible to avoid an increase in the wiring resistance. Therefore, it is possible to sufficiently ensure the ultrasonic wave detection sensitivity.

As described previously, the second conductive film 55 is separated from the upper electrode 26, so a gap 56 is formed between the second conductive film 44 and the upper electrode 26. The electrode separation film 43 inhibits the infiltration of moisture into the gap 56. As a result, even if the element unit 17 is exposed to moisture, it is possible to avoid electrical shorts between the upper electrode 26 and the second conductive film 55. In fact, since the electrode separation film 43 does not affect the edge of the vibrating film 24, the vibrating film 24 flexibility is maintained well. Therefore, it is possible to maintain the ultrasonic wave detection sensitivity.

The film thickness of the upper electrode 26 and the film thickness of the second conductive film 55 are equal. Therefore, it is possible to form the upper electrode 26 and the second conductive film 44 from one layer of conductive film. As will be described later, it is possible to form the upper electrode 26 and the second conductive film 55 with a shared manufacturing process. It is possible to simplify the manufacturing process.

The insulating film 44 stipulates that the two electrode separation films 43 sandwiching the second conductive body 31 and arranged at both sides of the second conductive body 31 be displaced in the direction separation from each other, so it is possible to increase the bonding strength of the electrode separation films 43. In addition, the insulating film 44 is formed on the surface of the base 21, so it is possible to increase the bonding strength of the insulating film 44. As a result, the bonding strength of the electrode separation film 43 is increased.

(4) Element Unit Manufacturing Method

Figure 6:
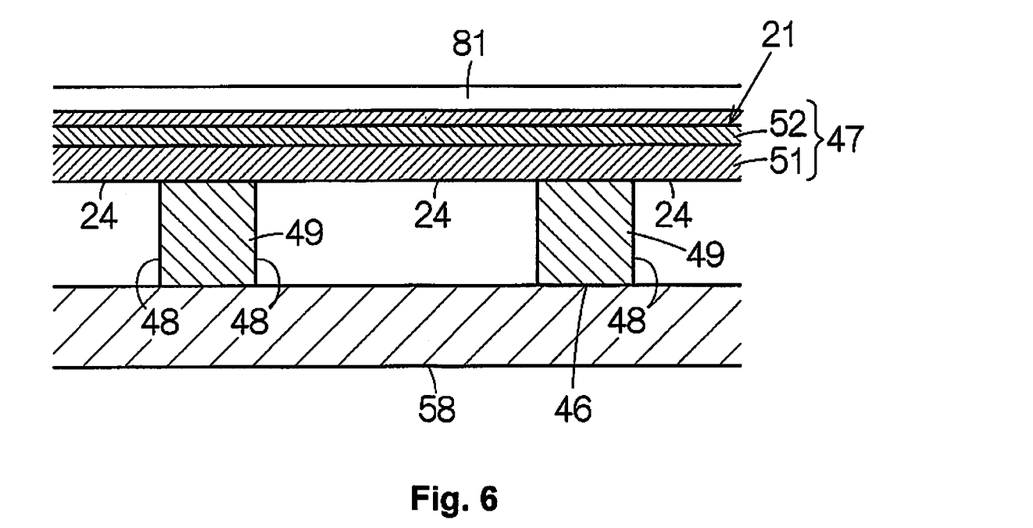
FIG. 6 is a cross section view schematically showing the formation process of the lower electrode and the first conductive film with the element unit manufacturing method corresponding to FIG. 4.

Next, we will give a brief description of the manufacturing method of the element unit 17. As shown in FIG. 6, the base 21 is prepared. The vibrating films 24 are arranged in an array pattern on the base 21. A first material film 81 is formed on the entire surface of the surface of the base 21. The first material film 81 has a uniform film thickness. The first material film 81 is formed from a conductive material. The first material film 81 is covered on the surface of the vibrating film 24.

The lower electrode 27 and the first conductive film 54 is formed from the first material film 81. Photolithography technology can be used for forming these. The lower electrode 27 and the first conductive film 54 are continuous with the surface of the base 21. At this point, the film thickness of the lower electrode 27 and the film thickness of the first conductive film 54 match.

Figure 7:
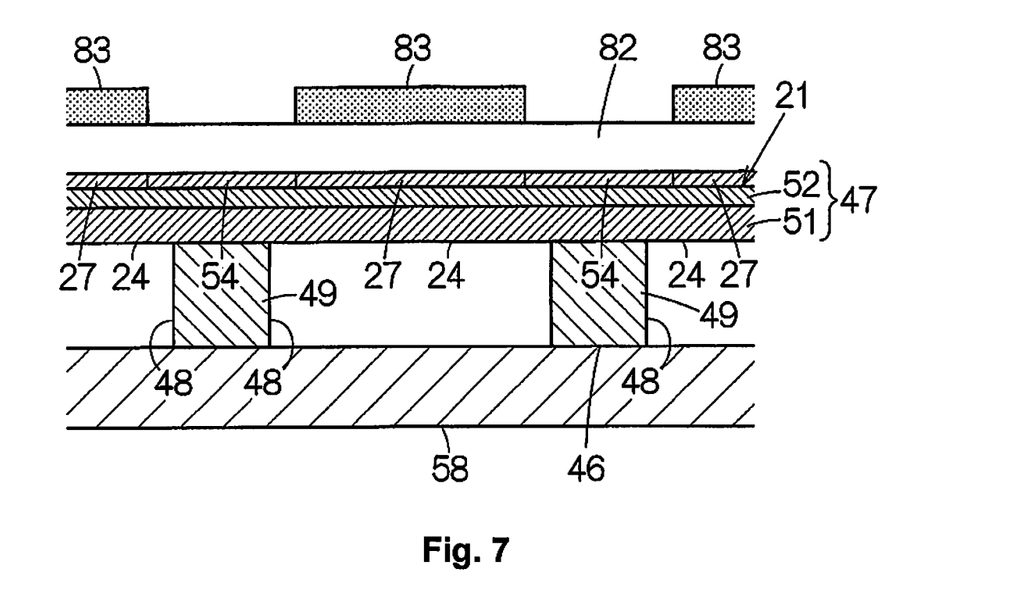
FIG. 7 is a cross section view schematically showing the formation process of the piezoelectric film with the element unit manufacturing method corresponding to FIG. 4.

Subsequently, the piezoelectric film 53 is formed on the vibrating film 24. As shown in FIG. 7, for forming of the piezoelectric film 53, a second material film 82 is formed on the entire surface of the surface of the base 21. The second material film 82 has a uniform film thickness. The second material film 82 is formed from a piezoelectric material. A resist film 83 is formed following a designated pattern on the second material film 82. Photo resist technology can be used for forming the resist film 83, for example. The resist film 83 is modeled on the shape of the piezoelectric film 53.

Figure 8:
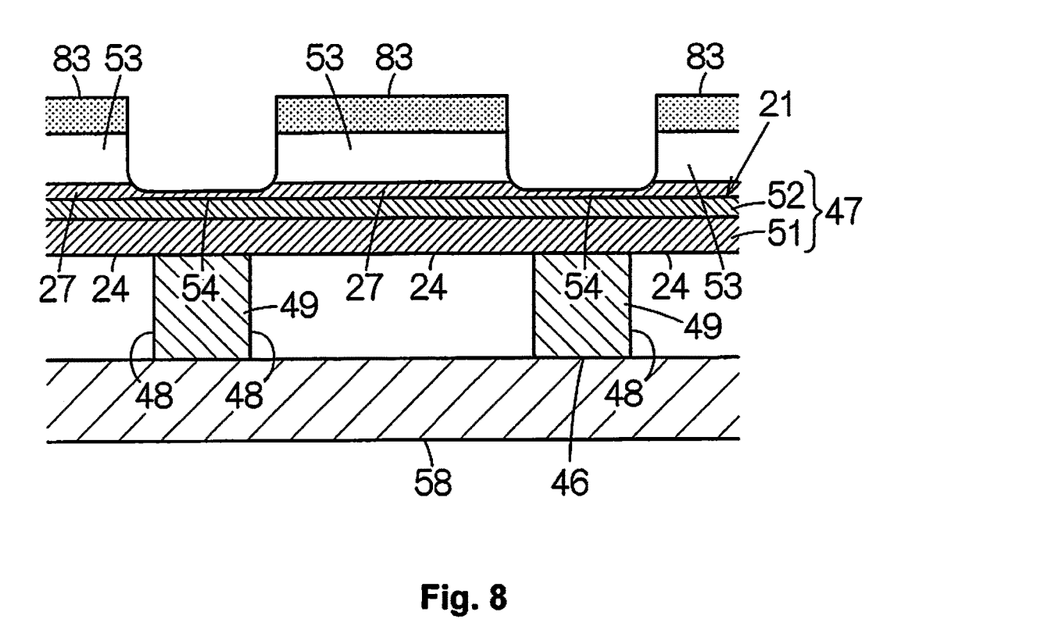
FIG. 8 is a cross section view schematically showing the etching processing process of the second material film with the element unit manufacturing method corresponding to FIG. 4.

As shown in FIG. 8, an etching process is implemented following a designated pattern on the second material film 82. The second material film 82 is removed at positions other than the resist film 83. In this way, the piezoelectric film 53 is formed from the second material film 82. At this time, the first conductive film 54 is scraped from the surface at positions other than the resist film 83. In this way, the film thickness of the first conductive film 54 becomes smaller than the film thickness of the lower electrode 27. When the etching process ends, the resist film 83 is removed.

Figure 9:
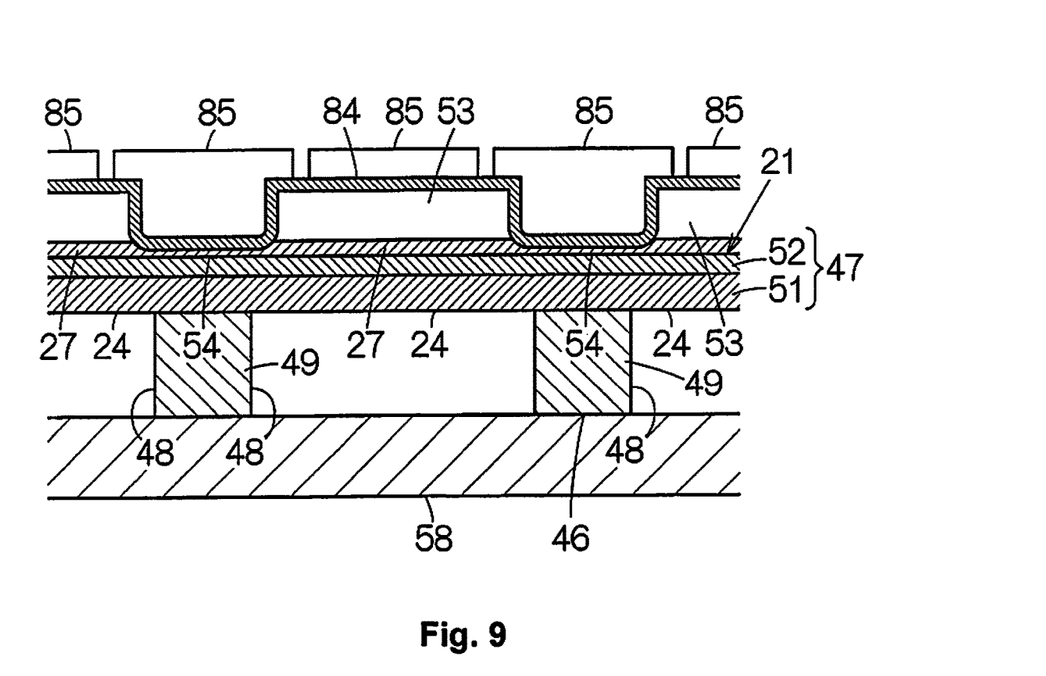
FIG. 9 is a cross section view schematically showing the formation process of the upper electrode and the second conductive film with the element unit manufacturing method corresponding to FIG. 4.

Subsequently, the upper electrode 26 is formed on the vibrating film 24. As shown in FIG. 9, for forming the upper electrode 26, a third material film 84 is formed on the entire surface of the surface of the base 21. The third material film 84 has a uniform thickness. The third material film 84 is formed from a conductive material. In this way, the third material film 84 is covered on at least the first conductive film 54 and the piezoelectric film 53 exposed surface. The film thickness of the first conductive film 54 increases. A resist film 85 is formed following a designated pattern on the third material film 84. Photo resist technology can be used for forming the resist film 85, for example. The resist film 85 is modeled on the shape of the upper electrode 27 and the second conductive film 55.

Figure 10:
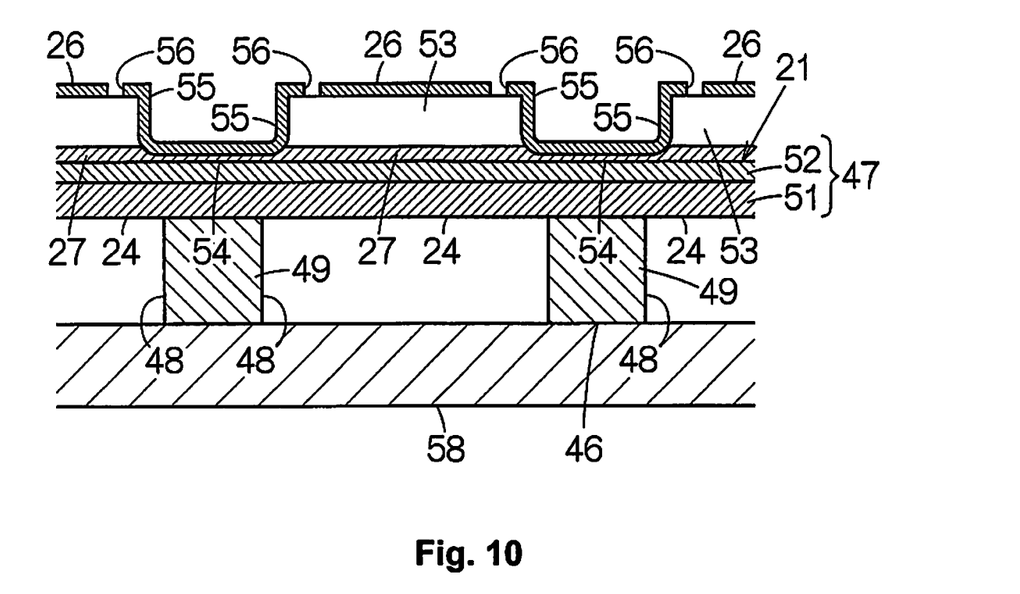
FIG. 10 is a cross section view schematically showing the formation process of the upper electrode and the second conductive film with the element unit manufacturing method corresponding to FIG. 4.

As shown in FIG. 10, etching processing is implemented following a designated pattern on the third material film 84. The third material film 84 is removed at positions other than the resist film 85. In this way, the upper electrode 26 and the second conductive film 55 are formed from the third material film 84. The outline of the upper electrode 26 is divided on the piezoelectric film 53. The second conductive film 55 is formed separated from the upper electrode 26 on the piezoelectric film 53. In this way, a gap 56 is formed with the third material film 84. The second conductive film 55 is separated from the upper electrode 26 by the gap 56. When etching processing ends, the resist film 85 is removed.

Figure 11:
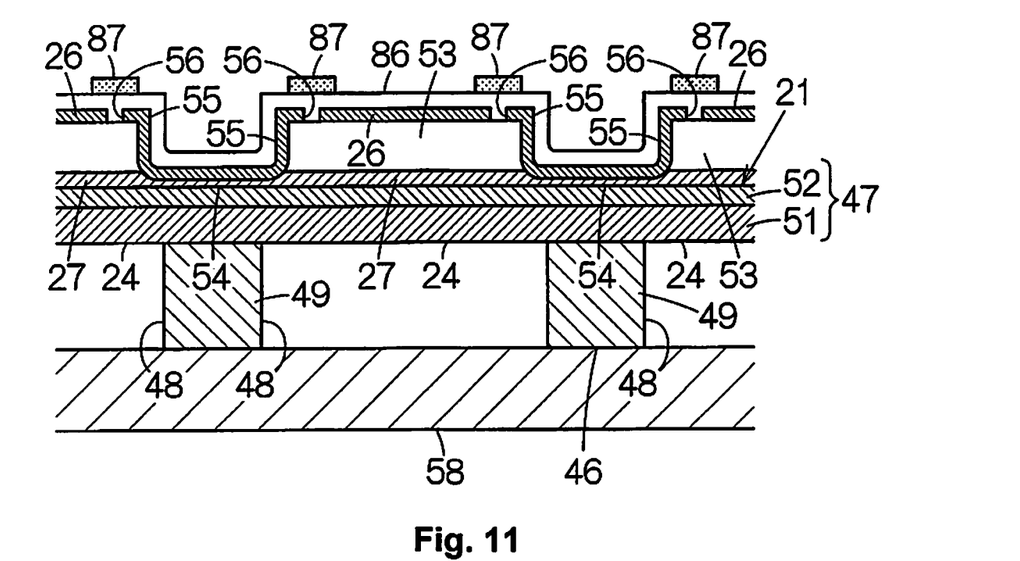
FIG. 11 is a cross section view schematically showing the formation process of the electrode separation film with the element unit manufacturing method corresponding to FIG. 4.

Subsequently, the electrode separation film 43 is formed on the vibrating film 24. As shown in FIG. 11, for forming the electrode separation film 43, a fourth material film 86 is formed on the entire surface of the surface of the base 21. The fourth material film 86 has a uniform film thickness. The fourth material film 86 is formed from an insulating material. The insulating material has moisture proof properties. The fourth material film 86 fills in at least the gap 56. A resist film 87 is formed following a designated pattern on the fourth material film 86. Photo resist technology can be used for forming the resist film 87, for example. The resist film 87 is modeled on the shape of the electrode separation film 43.

Etching processing is implemented following a designated pattern on the fourth material film 86. The fourth material film 86 is removed at positions other than the resist film 87. In this way, the electrode separation film 43 is formed from the fourth material film 86. When the etching processing ends, the resist film 87 is removed. After that, a protective film 57 is formed on the surface of the base 21. In this way, the element unit 17 is manufactured.

With the manufacturing method of this embodiment, etching processing is implemented for forming the piezoelectric film 53. At this time, in the periphery of the piezoelectric film 53, the first conductive film 54 is exposed by the etching process. As a result, the film thickness of the first conductive film 54 is smaller than the lower electrode 27. After that, the third material film 84 is layered on the first conductive film 54. In this way, the film thickness of the first conductive film 54 increases. It is possible to ensure sufficient film thickness for the wiring film connected to the lower electrode 27. It is possible to avoid an increase in the wiring resistance. Therefore, it is possible to sufficiently ensure ultrasonic wave detection sensitivity.

While the present embodiment has been explained in detail as above, it will be apparent to those skilled in the art that various changes and modifications can be made herein without substantially departing from the subject matter and the effect of the present invention. Therefore, such changes and modifications are included in the scope of the invention. For example, the terms used in the specification or the drawings at least once together with a different term having a broader or similar meaning can be replaced with the different term in any portion of the specification or the drawings. Also, the configurations and the operations of the ultrasonic diagnostic device 11, the ultrasonic probe 13, the probe head 13b, the element unit 17, the elements 23 and the like are not limited to the present embodiment, and various changes and modifications are possible.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer device comprising:
    a flexible film;
    a first conductive layer disposed on the flexible film;
    a piezoelectric layer disposed on the first conductive layer; and
    a second conductive layer disposed on the first conductive layer and the piezoelectric layer, wherein
    the first conductive layer includes a first portion facing the piezoelectric layer and a second portion which is not facing the piezoelectric layer,
    the second conductive layer includes a first portion facing the piezoelectric layer and a second portion isolated from the first portion of the second conductive layer,
    a total thickness of a thickness of the second portion of the first conductive layer and a thickness of the second portion of the second conductive layer is larger than a thickness of the first portion of the first conductive layer, and
    the thickness of the first portion of the first conductive layer is larger than the thickness of the second portion of the first conductive layer.

2. The ultrasonic transducer device according to claim 1, further comprising
    an insulating film disposed between the first portion of the second conductive layer and the second portion of the second conductive layer on the piezoelectric layer.

3. The ultrasonic transducer device according to claim 1, wherein
    a thickness of the first portion of the second conductive layer and the thickness of the second portion of the second conductive layer are substantially equal.

4. The ultrasonic transducer device according to claim 1, further comprising
    a partition wall formed on the flexible film on an opposite side of the piezoelectric layer to make an opening.

5. The ultrasonic transducer device according to claim 4, further comprising
    a reinforcing plate that closes the opening.

6. The ultrasonic transducer device according to claim 1, further comprising
    a protective film that covers the second conductive layer.

7. The ultrasonic transducer device according to claim 1, wherein
    the piezoelectric layer are arranged in a lattice manner.

8. The ultrasonic transducer device according to claim 1, wherein
    the second portion of the second conductive layer extends from the second portion of the first conductive layer to a surface of the piezoelectric layer.

9. A probe comprising:
    the ultrasonic transducer device according to claim 1; and
    a case supporting the ultrasonic transducer device.

10. An electronic instrument comprising:
    the ultrasonic transducer device according to claim 1; and
    a processing circuit connected to the ultrasonic transducer device, and configured to process output signals from the ultrasonic transducer device.

11. An ultrasonic image device comprising:
    the ultrasonic transducer device according to claim 1;
    a processing circuit connected to the ultrasonic transducer device, and configured to process output signals from the ultrasonic transducer device and generate an image; and
    a display device configured to display the image.

* * * * *